(12) United States Patent
Dean

(10) Patent No.: US 7,001,411 B1
(45) Date of Patent: Feb. 21, 2006

(54) SOFT TISSUE CLEAT

(76) Inventor: John C. Dean, 509 N. Garfield, Midland, TX (US) 79701

( * ) Notice: Subject to any disclaimer, the term of this patent is extended or adjusted under 35 U.S.C. 154(b) by 0 days.

(21) Appl. No.: 09/963,132

(22) Filed: Sep. 25, 2001

Related U.S. Application Data

(60) Provisional application No. 60/234,786, filed on Sep. 25, 2000.

(51) Int. Cl.
*A61B 17/04* (2006.01)
(52) U.S. Cl. .................. 606/232; 606/216; 606/220
(58) Field of Classification Search ............... 606/216, 606/220, 232
See application file for complete search history.

(56) References Cited

U.S. PATENT DOCUMENTS

| | | |
|---|---|---|
| 4,988,351 A | 1/1991 | Paulos et al. |
| 5,013,316 A | 5/1991 | Goble et al. |
| 5,167,665 A | 12/1992 | McKinney |
| 5,250,058 A | 10/1993 | Miller et al. |
| 5,306,290 A | 4/1994 | Martins et al. |
| 5,336,233 A | 8/1994 | Chen |
| 5,370,661 A | 12/1994 | Branch |
| 5,380,334 A | 1/1995 | Torrie et al. |
| D368,777 S | 4/1996 | Goble et al. |
| D374,286 S | 10/1996 | Goble et al. |
| D374,287 S | 10/1996 | Goble et al. |
| 5,601,558 A | 2/1997 | Torrie et al. |
| D404,128 S | 1/1999 | Huebner |
| 5,893,856 A | 4/1999 | Jacob et al. |
| 5,951,590 A | 9/1999 | Goldfarb |
| 6,036,704 A | 3/2000 | Yoon |
| 6,074,409 A | 6/2000 | Goldfarb |
| 6,093,201 A | 7/2000 | Cooper et al. |
| 6,096,060 A | 8/2000 | Fitts et al. |
| 6,206,886 B1 | 3/2001 | Bennett |

OTHER PUBLICATIONS

Craft, D.V., et al "Fixation Strength of Rotator Cuff Repairs With Suture Anchors and the Transosseous Suture Technique." Journal of Shoulder Elbow Surgery, vol. 5, No. 1 (Jan./Feb. 1996), pp. 32-40.

Rossouw, D.J., et al "A Biomechanical Evaluation of Suture Anchors in Repair of the Rotator Cuff." The Journal of Bone and Joint Surgery, vol. 79-B, No. 3 (May 1997), pp. 458-461.

Burkhart, S.S., et al "Cyclic Loading of Anchor-Based Rotator Cuff Repairs: Confirmation of the Tension Overload Phenomenom and Comparison of Suture Anchor Fixation with Transosseous Fixation." Arthroscopy: The Journal of Arthroscopic and Related Surgery, vol. 13, No. 6 (Dec. 1997), pp. 720-724.

Reed, S. C., et al "Full-Thickness Rotator Cuff Repairs—A Biomechanical Comparison of Suture Versus Bone Anchor Techniques." The American Journal of Sports Medicine, vol. 24, No. 1 (1996), pp. 46-48.

(Continued)

*Primary Examiner*—Gary Jackson
(74) *Attorney, Agent, or Firm*—Wong, Cabello, Lutsch, Rutherford & Brucculeri, LLP

(57) ABSTRACT

A method and soft tissue cleat device for improving the repair of soft tissue damage. A disc having projections pierces soft tissue and securely joins with a second disc to coapt the interposed soft tissue. This provides an increased pull-out strength of the suture and resistance to shear stresses, improving the quality of the repair. The present invention may be used with any bone fixation devices to reattach soft tissue to bone, and may also be used to rejoin soft tissues after a tear in the tissue.

35 Claims, 1 Drawing Sheet

OTHER PUBLICATIONS

Barber, F.A. et al "Suture Anchor Strength Revisited." Arthroscopy: The Journal of Arthroscopic and Related Surgery, vol. 12, No. 1, (Feb. 1996), pp. 32-38.

Barber, F.A., et al "Internal Fixation Strength of Suture Anchors—Update 1997." Arthroscopy: The Journal of Arthoscopic and Related Surgery, vol. 13, No. 3, (Jun. 1997), pp. 355-362.

Barber, F.A., et al "Suture Anchors—Update 1999." Arthroscopy: The Journal of Arthroscopic and Related Surgery, vol. 15, No. 7, (Oct. 1999), pp. 719-725.

Gerber, C., et al "Mechanical Strength of Repairs of the Rotator Cuff." The Journal of Bone and Joint Surgery, vol. 76-B, No. 3, (May 1994), pp. 371-380.

Gerber, C. "Experimental Rotator Cuff Repair," The Journal of Bone and Joint Surgery, vol. 81-A, No. 9, (Sep. 1999), pp. 1281-1290.

Goradia, V.K., et al "Cyclic Loading of Roator Cuff Repairs: A Comparison of Bioabsorbable Tacks With Metal Suture Anchors and Transosseous Sutures." Arthroscopy: The Journal of Arthroscopic and Related Surgery, vol. 17, No. 4, (Apr. 2001), pp. 360-364.

France, E.P. "Biomechanical Evaluation of Rotator Cuff Fixation Methods," The American Journal of Sports Medicine, vol. 17, No. 2, (1989), pp. 176-181.

Vermeiren, J., et al "Screw Fixation of a Complete Rotator Cuff Tear" Acta Orthopaedica Belgica, vol. 58, No. 1, (1992), pp. 88-90.

Robertson, D. B., et al "Soft Tissue Fixation to Bone" The American Journal of Sports Medicine, vol. 14, No. 5, (1986), pp. 398-403.

Straight, C.B., et al "Soft Tissue Fixation to Bone- A Biomechanical Analysis of Spiked Washers" The American Journal of Sports Medicine, vol. 22, No. 3, (1994), pp. 339-343.

Magen, H. E., et al "Structural Properties of Six Tibial Fixation Methods for Anterior Cruciate Ligament Soft Tissue Grafts" The American Journal of Sports Medicine, vol. 27, No. 1, (1999), pp. 35-43.

Burkhart, S.S., et al "Tissue Fixation Security in Transosseous Rotator Cuff Repairs: A Mechanical Comparison of Simple Versus Mattress Sutures" Arthroscopy: The Journal of Arthroscopic and Related Surgery, vol. 12, No. 6, (Dec. 1996), pp. 704-708.

Burkhart, S.S., et al "The Rotator Crescent and Rotator Cable: An Anatomic Description of the Shoulder's 'Suspension Bridge'" Arthroscopy: The Journal of Arthroscopic and Related Surgery, vol. 9, No. 6, (1993), pp. 611-616.

McLaughlin, H. L., "Lesions of the Musculotendinous Cuff of the Shoulder-The Exposure and Treatment of Tears with Retraction" Clinical Orthopaedics and Related Research No. 304, (1994), pp. 3-9.

SOFT TISSUE CLEAT

The present application claims the benefit of Provisional U.S. patent application Ser. No. 60/234,786 filed Sep. 25, 2000, which is hereby incorporated by reference. The benefit of 35 U.S.C. § 120 is claimed for the cited provisional patent application.

BACKGROUND OF THE INVENTION

1. Field of the Invention

The present invention relates generally to surgical devices and methods for repair of torn or avulsed soft tissue. More particularly, the present invention relates to a device and method for the secure fixation of torn or avulsed soft tissue to soft tissue and to bone.

2. Description of Related Art

It is not uncommon for tendons and other soft tissues to tear or detach from bone. Athletes, for example, often suffer orthopedic injuries such as torn or ruptured tendons and/or ligaments. For example, in the shoulder, a common injury is a torn rotator cuff in which a portion of the rotator cuff tendons tear within themselves or avulse from their insertion into bone. A torn rotator cuff can cause pain, weakness and loss of function.

In many cases, these symptoms can be relieved by surgically repairing the tear. This requires repairing any interstitial tears in the soft tissue (tendons, ligaments, and muscle) as well as approximating the torn edge of the soft tissue to the bone where it originated.

Current methods for reattaching soft tissue to bone use suture fixation, spiked soft tissue plates or staples at the torn edge of the tendon. Suture fixation of the tendon is the most common and classic method. In the case of tissue avulsing from bone, the torn free edge is typically debrided to clean up the edge before reattaching the edge to the bone. The torn free edge of the tendon, however, is usually poor quality tissue because it is usually involved in the degenerative process that is commonly involved in these tears. Improvements in the methods and devices to reattach soft tissue to bone have resulted in the soft tissue side of the repair when utilizing suture anchors becoming the weakest link of the overall construct.

Generally, in the repair of soft tissue, sutures are placed into soft tissue. A problem with this technique is pull-out of the sutures. It has also been observed that sutures applied to the tendon may strangulate and/or pull out the tendonous tissue. When this occurs, the suture material may stay intact but the tendon is connected to the bone through functionally insufficient scar tissue. This is particularly problematic in rotator cuff repairs, where scar tissue may limit mobility or reduce the strength of the soft tissue.

To lessen the risk of failure from pull-out of the sutures from the soft tissue, prior art methods incorporate various suture techniques and configurations. More complicated techniques such as the modified Mason-Allen stitch, call for weaving the suture back and forth in the tissue, accessing the more normal tissue proximal to the tear. While this is a stronger construct that the simple suture, there is a concern of strangulating the tissue with multiple weaves, resulting in necrosis of the tendon. Further, this technique does not lend itself to arthroscopic repair of the tear.

Other techniques used to combat the problem of suture tearing through tendon are limited to soft tissue buttons (as described in U.S. Pat. Nos. 5,306,290, 5,951,590 and 6,074,409, and the "TissueButton" by Arthrex), plates (as described in U.S. Pat. No. 6,093,201) or washers (as described U.S. Patent Nos. D0404128 and 6,206,886) that increase the effective surface area of the suture contact with the soft tissue and also aid in pressing the soft tissue against the bone at the repair interface. This type of tendon augmentation has been shown to resist failure perpendicular to the tendon fibers but does not reduce tendon shear parallel to the fibers, which is the failure mode when sutures tear through tendon.

There is also difficulty with suture placement in areas that are difficult to access surgically. In the case of rotator cuff injuries, traditional methods usually access the edge of the rotator cuff where tissue quality is poor. The more proximal tissue, which is generally healthier, is difficult to reach and usually not accessed.

Several other devices and techniques offer alternatives to suture fixation, including: screws, screws with spiked washers, plates, tacks, and staples. Screw and tack fixation have been shown to allow adequate fixation of tendon to bone. The soft tissue side of the repair is addressed by using either a broad flat head as part of the screw as in the "Headed Bio-Corkscrew" by Arthrex, or using a separate spiked washer to engage the soft tissue as in the "Biocuff" by Bionix. Tacks such as the smooth and spiked "Suretac" by Acufex address the soft tissue side identically. Patented devices in these categories include those described in U.S. Pat. Nos. 5,013,316, 5,380,334, 5,601,558, 5,370,661, 6,096,060, 5,167,665, 5,893,856 and 5,013,316. Spiked washer technology (such as described in U.S. Pat. Nos. 4,988,351, D0374287, D074482, D0374286 and D0368777) with screw fixation to bone has a long history in other applications such as knee ligament reconstruction and conceivably offers some advantage in resisting pull-out of the screw shank through those tendon fibers parallel to the direction of pull of the tendon. A common problem with the afore-mentioned technology is that the point of fixation of the soft tissue is at the free torn edge, which as noted above is poor quality.

Security of tissue fixation is an important element, particularly in rotator cuff repair. Current methods of obtaining fixation on the soft tissue side of the rotator cuff repair site are limited in their effectiveness by several factors. The free torn edge of the tendon is usually of relatively poor quality, as it is involved in the degenerative process leading to the tear. Arthroscopically placed simple sutures and all the non-suture devices discussed above gain fixation at this free torn edge. More complicated weaving sutures can overcome this problem by accessing more proximal tissue, which is healthier, thicker and stronger, but as noted above, this may be at the expense of tissue necrosis and does not lend itself to arthroscopic techniques.

It is therefore desirable to use a method, system, or device that improves the quality of soft tissue repair by utilizing the healthy areas of soft tissue, resisting shear forces, and increasing the pull-out strength of sutures. It is further desirable to employ a system or device that can be applied arthroscopically.

It is an object of the present invention to provide a method for improving the quality of soft tissue repair by using a soft tissue cleat capable of: attaching to strong, healthy soft tissue; distributing forces exerted on a suture over a larger area of the soft tissue; and increasing the pull-out strength of a suture.

It is another object of the present invention to provide a system for reducing stress on soft tissue by distributing forces over a larger area through the use of soft tissue cleats capable of gripping soft tissue and providing an attachment site for sutures.

It is another object of the present invention to provide a plurality of soft tissue cleats which may be configured to align or overlap along the soft tissue tear in such a way as to minimize stresses and forces at any given point or in any given area of the soft tissue.

SUMMARY OF THE INVENTION

In one respect, the present invention is directed to a method for applying a suture to soft tissue, comprising the steps of: coapting a first disc, the first disc having a plurality of projections and a hole defined therein, to a second disc, the second disc having a plurality of indentions defined therein to receive a portion of the peripheral projections of the first disc and having a hole defined therein, to coapt an area of soft tissue; securely joining the first disc to the second disc while maintaining a fixed distance between the first disc and the second disc; and passing a suture through the hole in first disc, the coapted area of soft tissue and the hole in the second disc. In a narrow respect, the present invention further describes a method wherein the step of securely joining the first disc to the second disc comprises mechanically locking a portion of each of the plurality of projections into the plurality of indentions in the second disc. In another narrow respect, the present invention further describes a method wherein the step of securely joining the first disc to the second disc comprises welding a portion of each of the plurality of projections to a portion of the second disc. In a narrower respect, welding a portion of each of the plurality of projections to a portion of the second disc uses ultrasonic energy. In a narrower respect, welding a portion of each of the plurality of projections to a portion of the second disc uses thermal energy.

In another broad respect, the present invention is directed to a soft tissue cleat, for coapting soft tissue, comprising: a first disc having a hole that is larger in size than a suture and a plurality of fixed-length projections extending perpendicularly from the bottom surface of the first disc; a second disc having a hole that is larger in size than the suture, and having a plurality of indentions, the plurality of indentions being configured to receive a portion of said plurality of projections; wherein the plurality of fixed-length projections of the first disc is configured to perforate soft tissue and to securely join to the second disc; and wherein the hole in the first disc is aligned with in the second disc when the first disc is securely joined to the second disc to permit passage of a suture therethrough. In a narrow respect, the hole in the first disc is located proximate to the center of the first disc. In another narrow respect, the hole in the second disc is located proximate to the center of the first disc. In another narrow respect, each of the plurality of indentions in the second disc comprises a mechanical locking mechanism for securely joining each of the plurality of fixed-length projections to the second disc. In another narrow respect, each of the plurality of projections is configured to be welded to the second disc. In a narrower respect, each of the plurality of projections is configured to be welded to the second disc with ultrasonic energy. In another narrower respect, each of the plurality of projections is configured to be welded to the second disc with thermal energy. In yet another narrow respect, the first disc, second disc, and plurality of projections are each made from radiolucent material. In yet another narrow respect, the first disc, second disc, and plurality of projections are each made from bioabsorbable material. In yet another narrow respect, the first disc, second disc, and plurality of projections are each made from non-bioabsorbable material.

In another broad respect, the present invention is directed to a soft tissue cleat, for coapting soft tissue, comprising: a first disc having a plurality of fixed-length projections extending perpendicularly from the bottom surface of the first disc and having a first suture coupled to a portion of the top surface of the first disc; a second disc having a plurality of indentions extending inward from the top surface of the second disc, the plurality of indentions being configured to receive a portion of said plurality of projections, and the second disc having a second suture coupled to a portion of the bottom surface of the second disc; wherein the plurality of fixed-length projections of the first disc is configured to perforate soft tissue and to securely join to the second disc. In a narrow respect, each of the plurality of indentions in the second disc comprises a mechanical locking mechanism for securely joining each of the plurality of fixed-length projections to the second disc. In another narrow respect, each of the plurality of projections is configured to be welded to the second disc. In a narrower respect, each of the plurality of projections is configured to be welded to the second disc with ultrasonic energy. In another narrower respect, each of the plurality of projections is configured to be welded to the second disc with thermal energy. In yet another narrow respect, the first disc, second disc, and plurality of projections are each made from radiolucent material. In yet another narrow respect, the first disc, second disc, and plurality of projections are each made from bioabsorbable material. In yet another narrow respect, the first disc, second disc, and plurality of projections are each made from non-bioabsorbable material.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Classically, when soft tissue is torn or avulsed from bone, it is repaired by suture fixation. This applies to many orthopedic injuries such as torn or ruptured tendons and ligaments. In the shoulder, a common injury is a torn rotator cuff in which any portion of the rotator cuff tendons tear within themselves or avulse from their insertion into bone. The embodiments of the present invention described below will be discussed with respect to the torn rotator cuff model. However, it is noted that the device embodying the present invention may be applied to the entire spectrum of orthopedic injuries where soft tissue is torn or avulsed from bone.

Devices embodying the present invention overcomes prior techniques for repairing soft tissue injuries. In particular, with embodiments of the present invention, forces are distributed over a much larger surface area than existing techniques, and thus are more able to resist shear forces, and prevent pull-out of sutures.

Figure 1:
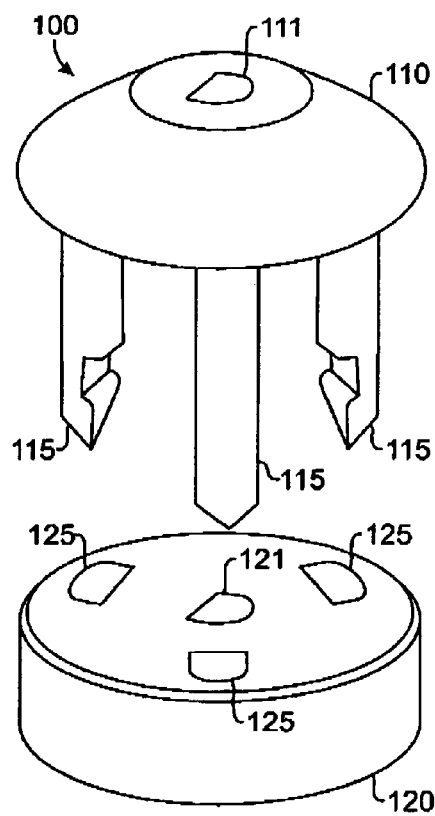
FIG. 1 is a perspective view of a soft tissue cleat in accordance with one embodiment of the present invention.

FIG. 1 illustrates a soft tissue cleat device that may be used in soft-tissue repair, according to one embodiment of the present invention. As shown, the device comprises two discs that capture the interposed soft tissue when joined together. The grasping disc 110 has a plurality of peripheral projections 115 that are designed to pierce the soft tissue. The locking disc 120 has a corresponding number of holes 125 for receiving the peripheral projections 115. Each hole 125 may have a mechanical locking mechanism to hold the peripheral projection 115, locking the two discs together, firmly capturing the interposed rotator cuff tissue. In other embodiments (not shown), the two discs may be fixed together by welding the peripheral projections 115 to locking disc 120, such as by thermal or ultrasonic means. Once peripheral projections 115 from the grasping disc 110 engage holes 125 in locking disc 120, the assembly becomes a fixed soft tissue cleat 100.

Figure 2:
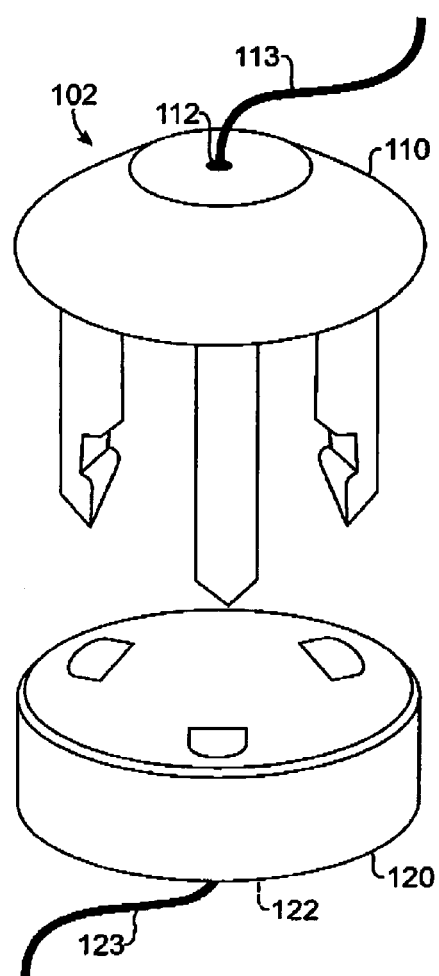
FIG. 2 is a perspective view of a soft tissue cleat in accordance with another embodiment of the present invention.

In addition, the soft tissue cleat 100 has a mechanism for attaching a suture. As shown, the grasping disc 110 has a central hole 111 and the locking disc 120 has a central hole 121 for passing a suture through the center of the fixed soft tissue cleat 100. Alternatively, in some embodiments, such as cleat 102 shown in FIG. 2, a suture 113/123 may be attached to one or both discs 110/120 at 112/122, eliminating the need to pass the suture through central holes, such as holes 111 and 121 of FIG. 1. Advantageously, these embodiments, such as cleat 102, may be desirable in situations where the soft tissue cleat 102 is not easily accessible for passing a suture through a center hole.

Though three peripheral projections 115 are shown, the present invention is not so limited. The length, shape, number, and configuration of barbed projections 115 are design decisions primarily to ensure that the interposed soft tissue is not compressed to a degree sufficient to cause necrosis, while at the same time effectively distributing forces (including shear forces and stresses) throughout the soft tissue to avoid comprising the integrity of the structure. In some embodiments, the number of peripheral projections 115 per implant that optimizes fixation while minimizing soft tissue injury is between three and six, inclusive.

The soft tissue cleat 100 and the components thereof may be made from any biocompatible material. The particular material that is used is a design decision that depends on the particular application of soft tissue cleat 100. By way of illustration and not limitation, it is noted that in some embodiments, it may be desirable for soft tissue cleat 100 to be made from radiolucent, non-metallic materials, such as any of the nonmetallic polymers used in orthopedics. One example is polyethylene. Further, in some situations, bioabsorbable materials should be used. An advantage of using a bioabsorbable material is that chronic stress shielding of the soft tissue by the soft tissue cleat 100 would be reduced. In one particular embodiment, a bioabsorbable soft tissue cleat is used in conjunction with a nonabsorbable suture. However, in other embodiments, metallic cleats may be desirable. For example, a titanium implant has advantages over a nonmetallic implant, such as the increased ability of titanium peripheral projections 115 to penetrate the soft tissue without breaking.

The overall size, shape and design of discs 110 and 120 are a design decision and may vary based on many factors related to the particular medical application. Generally, however, as shown in FIG. 1, it is preferable that the cleat 100 have low profile with a smooth transition at the junction of the grasping disc 110 and interposed soft tissue to reduce complications. For example, in rotator cuff repair, one of the potential risks with using a cleat would be impingement against the acromion or superior glenoid that could generate pain or mechanical symptoms such as catching or locking.

Generally, a soft tissue tear has an associated area of poor quality tissue on either side. Placement of soft tissue cleats 100 in healthy tissue is a preferred method for repairing soft tissue injuries. Once the soft tissue cleat is in place, a suture can then be applied, and affixed to the soft tissue cleat to improve the overall quality of the repair. In general, the coapting discs are placed proximal to the poor-quality torn free edge of the torn tendon or muscle. This more proximal tissue, termed the "rotator cable," is quite substantial, averaging 2.59 times the thickness of the tendon distal to this, where most convention techniques gain fixation.

It is also important that the soft tissue in between the two halves of the soft tissue cleat 100 not be subjected to too much pressure. Too much pressure may deprive the soft tissue of its blood supply, which may lead to necrosis and loss of fixation of the cleat 100. Therefore, a key design concept for the cleat 100 is to limit the compression of the soft tissue while keeping enough pressure to maintain fixation. Multiple grasping discs 110 may be designed having peripheral projections 115 of various lengths. Accordingly, the desired grasping disc 110 having peripheral projections 115 of the necessary length to maintain the desired amount of compression may be used.

In some embodiments, not shown, a system of soft tissue cleats 100 may be used to address massive soft tissue tears, such as may be found in a rotator cuff tear. In these embodiments, larger cleats may be placed more proximal with more than one suture originating from each. These sutures may then engage other small implants nearer to the free edge of the tear. Each of these smaller cleats would receive suture input from several of the larger, more proximal cleats, emulating the structure of a trestle, helping to distribute loads evenly.

The soft tissue cleats embodying the present invention are compatible with any and all of the conventional methods or devices to affix soft tissue to bone. Examples include, but are not limited to, suture anchors, sutures through bone tunnels, tacks and screws. Advantageously, the soft tissue side of the repair (often the weakest point of a repair structure) may be reinforced independently of the method of bone fixation.

The preceding examples are included to demonstrate specific embodiments of the invention. It should be appreciated by those of skill in the art that the techniques disclosed in the examples which follow represent techniques discovered by the inventor to function well in the practice of the invention, and thus can be considered to constitute preferred modes for its practice. However, it should be understood that the invention is not intended to be limited to the particular forms disclosed. Rather, the different aspects of the disclosed compositions and methods may be utilized in various combinations and/or independently. Thus the invention is not limited to only those combinations shown herein, but rather may include other combinations. Further, those of skill in the art should, in light of the present disclosure, appreciate that many changes can be made in the specific embodiments which are disclosed and still obtain a like or similar result without departing from the spirit and scope of the invention.

REFERENCES

The following references, to the extent that they provide exemplary procedural or other details supplementary to those set forth herein, are specifically incorporated herein by reference.

H. L. McLaughlin, Lesions of the Musculotendinous Cuff of the Shoulder, Journal of Bone and Joint Surgery Am, 1978; 26-A: 31–51.

David Craft, et al, Fixation Strength of Rotator Cuff Repairs With Suture Anchors and the Transosseous Suture Technique, Journal of Shoulder and Elbow Surgery, 1996, 5(1): 32–40.

D. J. Rossouw, et al, A Biomechanical Evaluation of Suture Anchors in Repair of the Rotator Cuff, Journal of Bone and Joint Surgery Br, 1997; 79-B: 458–61.

S. S. Burkhart, et al, Cyclic Loading of Anchor Based Rotator Cuff Repairs: Confirmation of the Tension Overload Phenomenon and Comparison of Suture Anchor Fixation With Transosseous Fixation, Arthroscopy, 1997, 13(6): 704–8.

S. C. Reed, et al, Full-Thickness Rotator Cuff Tears, A Biomechanical Comparison of Suture Versus Bone Anchor Techniques, The American Journal of Sports Medicine, 1996, 24(1): 46–48.

F. A. Barber, et al, Suture Anchors-Update 1999, Arthroscopy, 1999, 15(7): 719–725.

F. A. Barber, et al, Internal Fixation Strength of Suture Anchors-Update 1997, Arthroscopy, 1997, 13(3): 355–362.

F. A. Barber, et al, Suture Anchor Strength Revisited, Arthroscopy, 1996, 12(1): 32–38.

Christian Gerber, et al, Mechanical Strength of Repairs of the Rotator Cuff, Journal of Bone and Joint Surgery Br, 1994, 76-B: 371–80.

Christian Gerber, et al, Experimental Rotator Cuff Repair, Journal of Bone and Joint Surgery Am, 1999, 81-A: 1281–90.

E. Paul France, et al, Biomechanical Evaluation of Rotator Cuff Fixation Methods, The American Journal of Sports Medicine, 1989, 17(2): 176–181.

J. Vermeiren, et al, Screw Fixation of a Complete Rotator Cuff Tear, Acta Orthopaedica Belgica, 1992, 58(1): 88–90.

Daniel B. Robertson, et al, Soft Tissue Fixation to Bone, The American Journal of Sports Medicine, 1986, 14(5): 398–403.

C. B. Straight, et al, Soft Tissue Fixation to Bone-A Biomechanical Analysis of Spiked Washers, The American Journal of Sports Medicine, 1994, 22(3): 339–343.

Hugh E. Magen, Structural Properties of Six Tibial Fixation Methods for Anterior Cruciate Ligament Soft Tissue Grafts, The American Journal of Sports Medicine, 1999, 27(1): 35–43.

Stephen S. Burkhart, et al, Tissue Fixation Security in Transosseous Rotator Cuff Repairs: A Mechanical comparison of Simple Versus Mattress Sutures, Arthroscopy, 1996, 12(6): 704–708.

Stephen S. Burkhart, et al, The Rotator Crescent and Rotator Cable: An Anatomic Description of the Shoulder's "Suspension Bridge", Arthroscopy, 9(6): 611–616.

What is claimed is:

1. A method for applying a suture to soft tissue, comprising the steps of:
   coapting a first disc, the first disc having a plurality of projections and a hole defined therein, to a second disc, the second disc having a plurality of indentations therein to receive a portion of the projections of the first disc and having a hole defined therein, to coapt an area of soft tissue;
   securely joining the first disc to the second disc while maintaining a fixed distance between the first disc and the second disc; and
   passing a suture through the hole in the first disc, the coapted area of soft tissue and the hole in the second disc.

2. The method of claim 1, wherein the step of securely joining the first disc to the second disc comprises mechanically locking a portion of each of the plurality of projections into the plurality of indentations in the second disc.

3. The method of claim 1, wherein the step of securely joining the first disc to the second disc comprises welding a portion of each of the plurality of projections to a portion of the second disc.

4. The method of claim 3, wherein said welding uses ultrasonic energy.

5. The method of claim 3, wherein said welding uses thermal energy.

6. A soft tissue cleat, for coapting soft tissue, comprising:
   a suture for the cleat;
   a first disc having a hole that is larger in size than the suture for passage of the suture, the first disc having a plurality of fixed-length projections extending perpendicularly from the bottom surface of the first disc; and
   a second disc having a hole that is larger in size than the suture for passage of the suture, the second disc having a plurality of indentations, the plurality of indentations being configured to receive a portion of said plurality of projections;
   wherein the plurality of fixed-length projections of the first disc is configured to perforate soft tissue and to securely join to the second disc;
   wherein the hole in the first disc is aligned with in the second disc when the first disc is securely joined to the second disc to permit passage of the suture therethrough.

7. The device of claim 6, wherein the hole in the first disc is located proximate to the center of the first disc.

8. The device of claim 6, wherein the hole in the second disc is located proximate to the center of the first disc.

9. The device of claim 6, wherein each of the plurality of indentations in the second disc comprises a mechanical locking mechanism for securely joining each of the plurality of fixed-length projections to the second disc.

10. The device of claim 6, wherein each of the plurality of projections is configured to be welded to the second disc with ultrasonic energy or with thermal energy.

11. The device of claim 6, wherein the first disc, second disc, and plurality of projections are each made from radiolucent material, bioabsorbable material, or non-bioabsorbable material.

12. The device of claim 6, wherein each of the plurality of projections is configured to be welded to the second disc.

13. A soft tissue cleat, for coapting soft tissue, comprising:
    a first disc having a plurality of fixed-length projections extending perpendicularly from the bottom surface of the first disc and having a first suture coupled to a portion of the top surface of the first disc; and
    a second disc having a plurality of indentations extending inward from the top surface of the second disc, the plurality of indentations being configured to receive a portion of said plurality of projections, and the second disc having a second suture coupled to a portion of the bottom surface of the second disc;
    wherein the plurality of fixed-length projections of the first disc is configured to perforate soft tissue and to securely join to the second disc.

14. The device of claim 13, wherein each of the plurality of indentations in the second disc comprises a mechanical locking mechanism for securely joining each of the plurality of fixed-length projections to the second disc.

15. The device of claim 13, wherein each of the plurality of projections is configured to be welded to the second disc.

16. The device of claim 15, wherein each of the plurality of projections is configured to be welded to the second disc with ultrasonic energy.

17. The device of claim 15, wherein each of the plurality of projections is configured to be welded to the second disc with thermal energy.

18. The device of claim 13, wherein the first disc, second disc, and plurality of projections are each made from radiolucent material.

19. The device of claim 13, wherein the first disc, second disc, and plurality of projections are each made from bioabsorbable material.

20. The device of claim 13, wherein the first disc, second disc, and plurality of projections are each made from non-bioabsorbable material.

21. A cleat for coapting soft tissue, comprising:
   a suture for the cleat;
   a first disc having a hole therethrough for passage of the suture, the first disc having a first surface for positioning against one side of the soft tissue and having a plurality of projections, each projection extending from the first surface and having a first locking mechanism; and
   a second disc having a hole therethrough for passage of the suture, the second disc having a second surface for positioning against another side of the soft tissue and having a plurality of second locking mechanisms, the second locking mechanisms configured to engage the first locking mechanisms of the projections,
   wherein the engagement between the first and second locking mechanisms securely join the projections to the second disc and maintains a fixed distance between the first and second surfaces of the first and second discs.

22. The cleat of claim 21, wherein each of the projections comprises a distal end for perforating the soft tissue and a proximal end attached to the first surface.

23. The cleat of claim 22, wherein each first locking mechanism comprises a first locking surface defined in the projection adjacent the distal end and a second locking surface defined in the projection adjacent the proximal end.

24. The cleat of claim 21, wherein each of the plurality of projections is configured to be welded to the second disc with ultrasonic energy or with thermal energy.

25. The cleat of claim 21, wherein the first disc, second disc, and plurality of projections each comprise radiolucent material, bioabsorbable material, or non-bioabsorbable material.

26. A cleat for coapting soft tissue, comprising:
   a first disc having a first surface for positioning against one side of the soft tissue and having a plurality of projections, each projection extending from the first surface and having a first locking mechanism; and
   a second disc having a second surface for positioning against another side of the soft tissue and having a plurality of second locking mechanisms, the second locking mechanisms configured to engage the first locking mechanisms of the projections,
   wherein the engagement between the first and second locking mechanisms securely join the projections to the second disc and maintains a fixed distance between the first and second surfaces of the first and second discs,
   wherein the first disc comprises a first portion of suture attached to the first disc, and
   wherein the second disc comprises a second portion of suture attached to the second disc.

27. The cleat of claim 26, wherein each of the projections comprises a distal end for perforating the soft tissue and a proximal end attached to the first surface.

28. The cleat of claim 27, wherein each first locking mechanism comprises a first locking surface defined in the projection adjacent the distal end and a second locking surface defined in the projection adjacent the proximal end.

29. The cleat of claim 26, wherein each of the plurality of projections is configured to be welded to the second disc with ultrasonic energy or with thermal energy.

30. The cleat of claim 26, wherein the first disc, second disc, and plurality of projections each comprise radiolucent material, bioabsorbable material, or non-bioabsorbable material.

31. A cleat for coapting soft tissue, comprising:
   a first disc having a first surface for positioning against one side of the soft tissue and having a plurality of projections, each projection extending from the first surface and having a first locking mechanism;
   a portion of suture attached to the first disc; and
   a second disc having a second surface for positioning against another side of the soft tissue and having a plurality of second locking mechanisms, the second locking mechanisms configured to engage the first locking mechanisms of the projections,
   wherein the engagement between the first and second locking mechanisms securely join the projections to the second disc and maintains a fixed distance between the first and second surfaces of the first and second discs.

32. The cleat of claim 31, wherein each of the projections comprises a distal end for perforating the soft tissue and a proximal end attached to the first surface.

33. The cleat of claim 32, wherein each first locking mechanism comprises a first locking surface defined in the projection adjacent the distal end and a second locking surface defined in the projection adjacent the proximal end.

34. The cleat of claim 31, wherein each of the plurality of projections is configured to be welded to the second disc with ultrasonic energy or with thermal energy.

35. The cleat of claim 31, wherein the first disc, second disc, and plurality of projections each comprise radiolucent material, bioabsorbable material, or non-bioabsorbable material.

* * * * *